United States Patent [19]

Haber

[11] Patent Number: 4,786,276

[45] Date of Patent: Nov. 22, 1988

[54] TRIPLE CUSHION SPHINCTERIC WEB

[75] Inventor: Terry M. Haber, Lake Forest, Calif.

[73] Assignee: Habley Medical Technology Corporation, Laguna Hills, Calif.

[21] Appl. No.: 68,421

[22] Filed: Jul. 1, 1987

[51] Int. Cl.[4] .............................................. A61B 19/00
[52] U.S. Cl. ............................. 600/31; 128/DIG. 26; 623/14
[58] Field of Search ............... 128/1 R, 346, DIG. 25; 623/11, 14; 600/29-31

[56] References Cited

U.S. PATENT DOCUMENTS

| | | | |
|---|---|---|---|
| 3,866,611 | 2/1975 | Baumrucker | 128/DIG. 25 |
| 3,903,894 | 9/1975 | Rosen et al. | 128/DIG. 25 |
| 4,428,365 | 1/1984 | Hakky | 128/DIG. 25 |
| 4,634,443 | 1/1987 | Haber | 128/DIG. 25 |

Primary Examiner—Dalton L. Truluck
Attorney, Agent, or Firm—Morland C. Fischer

[57] ABSTRACT

A sphincteric web for the treatment of incontinence having a particular alignment of three inflatable pressure cushions by which to prosthetically replicate the geometry of a normally continent rectum. The sphincteric web surrounds and embraces a patient's colon (or rectum), and the pressure cushions are inflated with hydraulic fluid from a hypodermically accessible source thereof. The inflated pressure cushions produce axial, deflective forces which closely mimic the three valvular deflections produced by the rectal valves in a healthy anatomy. Accordingly, the patient's colon is deflected, rather than constricted or obstructed, to increase the resistance to the flow of waste material and thereby return the patient to continence.

10 Claims, 5 Drawing Sheets

4,786,276

TRIPLE CUSHION SPHINCTERIC WEB

BACKGROUND OF THE INVENTION

1. Field of the Invention

This invention relates to a sphincteric web for the treatment of incontinence having three inflatable cushions by which to prosthetically replicate the geometry of a normally continent rectum and, thereby, return the patient to continence.

2. Prior Art

In a colostomy or ileostomy patient, some or all of the large intestine may have been removed due to cancer, inflamatory bowel disease, and other infectious causes requiring excision and resection. Surgically implantable prosthetic sphincters are known by which to treat colostomy or ileostomy patients for incontinence. However, conventional artificial sphincters commonly include an occlusion cuff which surrounds and squeezes the colon to achieve continence through the application of equal and opposite forces in a single plane. Such coplanar force-generating sphincters act to constrict the colon so as to create an obstruction for blocking the flow of waste material therethrough.

However, by constricting or squeezing the colon to achieve continence, blood flow through the patient's delicate tissues may be undesirably interrupted or impeded. Consequently, there exists a likelihood that the patient will be susceptible to hypertrophy, ischemia, necrosis and/or erosion, thereby requiring further surgery and the removal or adjustment of the sphincter.

Examples of conventional artificial sphincters which include a plurality of inflatable chambers by which to treat incontinence may be found by referring to either of U.S. Pat. Nos. 4,399,809 issued Aug. 23, 1983 or 4,428,365 issued Jan. 31, 1984.

SUMMARY OF THE INVENTION

Briefly, a sphincteric web is disclosed for the treatment of incontinence. The sphincteric web is particularly adapted to surround and embrace the colon (or rectum) of a colostomy or ileostomy patient where some or all of the large intestine has been removed due to cancer or infectious disease and/or the natural sphincter muscles are rendered functionally inoperative due to age, trauma, or sphincteric dysfunction. The sphincteric web has three inflatable pressure cushions which are aligned with one another so as to prosthetically replicate the geometry of a normally continent rectum. That is to say, with the sphincteric web surrounding the colon, the pressure cushions are inflated with hydraulic fluid to produce axial, deflective forces which closely mimic the valvular deflections produced by the rectal valves of a healthy anatomy.

When the pressure cushions are inflated, the deflective forces applied to the colon are directed in respective planes that are aligned transvesely to the orientation of the colon. More particularly, the pressure cushions are spaced longitudinally from one another, such that no two of the deflective forces produced thereby are applied to the colon in the same plane. Such non-coplanar forces establish a deflection of the colon to restrict the movement of material therethrough.

A pair of pressure cushions are positioned at opposite sides of the sphincteric web in alignment with each other and the longitudinal axis of the web. The third of the pressure cushions is positioned at one end of the web and in alignment with the lateral axis thereof. The sphincteric web is implanted in a perianal location with a plane created by the center line of the pressure cushions oriented in anterior-posterior midline alignment. A pair of buttons is formed at one end and a pair of buttonholes is formed at the opposite end of the sphincteric web. The sphincteric web is folded around the patient's colon and the opposite ends of the web are connected together by inserting the buttons through the buttonholes.

By virtue of the present sphincteric web, the patient's colon is deflected, rather than constricted or obstructed, to increase the resistance to material flow and thereby return the patient to continence. Moreover, such deflection is accomplished by means of the non-planar geometry of the pressure cushions so as to avoid the possibility of strangulating the colon, whereby to reduce the likelihood of hypertrophy, ischemia, necrosis and/or erosion.

DESCRIPTION OF THE PREFERRED EMBODIMENT

Figure 1:
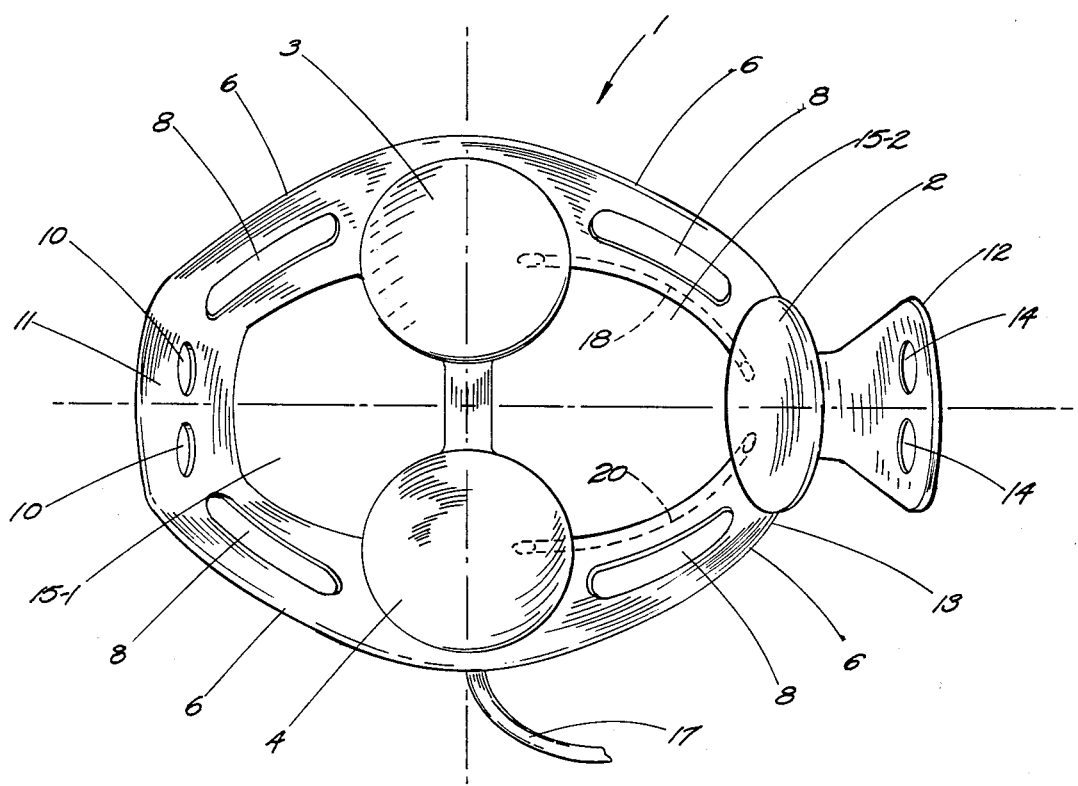
FIG. 1 is a bottom view of the triple cushion sphincteric web which forms the present invention.

Referring now to the drawings, there is shown in FIG. 1 a sphincteric web 1 which forms the prosthetic sphincter of the present invention. Sphincteric web 1 comprises a plurality of (e.g. three) inflatable, hemi-spheric pressure cushions 2, 3 and 4. As will be explained in greater detail hereinafter, the pressure cushions 2, 3 and 4 are controllably inflated to prosthetically deflect the colon of an incontinent colostomy or ileostomy patient, whereby to return a patient to continence by mimicing the natural deflective forces which would normally be provided by the patient's rectal valves. Pressure cushions 3 and 4 are positioned at opposite sides of web 1 (along the longitudinal axis thereof). Pressure cushion 2 is positioned at one end of the web (along the lateral axis thereof). In this manner and as will be understood when referring to FIG. 9, the sphincter web 1 will be able to artificially replicate the geometry of a normally continent rectum when the web is attached around the patient's colon.

As will be known to those skilled in the art, the rectal valves may be rendered functionally inoperative or may require excision (along with the patient's rectum) as a consequence of cancer, inflamatory bowel disease, trauma, age, or other sphincteric dysfunction. Inamuch as there are three rectal valves in the human anatomy (i.e., the superior, medial, and inferior rectal valves), sphincteric web 1 is preferably provided with three pressure cushions 2, 3 and 4. However, the precise number of pressure cushions utilized could be varied according to the tissue requirements of a particular patient.

The inflatable pressure cushions 2, 3 and 4 are maintained in a desired alignment with one another by a flexible, minimally extensible positioning and tensile resistant webbing 6 to which the pressure cushions are attached. Webbing 6 is preferably fabricated from a polyester based, bicompatible, silicon reinforced mesh. One or more slots 8 may be formed in the webbing 6 to increase the flexibility thereof. Webbing 6 has a pair of buttonholes 10 formed through a primary fastening end 11 thereof. An optional closure tab 12, also having a pair of buttonholes 14 formed therethrough, is coextensively formed with an extended outwardly from a secondary fastening end 13 of webbing 6 at a location adjacent one of the pressure cushions 2. A pair of buttons (designated 22 in FIGS. 2 and 3) is formed at the top of pressure cushion 2. The purpose of buttonholes 10 and 14 and buttons 22 will be described when referring to FIGS. 2 and 3.

The periphery of webbing 6 surrounds adjacent primary and secondary openings 15-1 and 15-2. The openings are separated from one another by a longitudinally extending linking member 16. Linking member 16 also mechanically connects and supports a pair of pressure cushions 3 and 4. The presence of primary and secondary openings 15-1 and 15-2 maximizes the flexibility of and permits sphincteric web 1 to be folded around a patient's colon in a manner which will soon be disclosed.

A fluid circuit for controllably inflating (or deflating) the pressure cushions 2, 3 and 4 of sphincteric web 1 is now disclosed while continuing to refer to FIG. 1. Fluid is transferred into and out of the pressure cushions 2, 3 and 4 by way of flexible, non-kinking hydraulic tubing 17. Hydraulic tubing 17 extends between a source of hydraulic fluid (e.g. a radio opaque, physiological saline solution, or the like) and one of the inflatable pressure cushions 4. One example of a suitable fluid source is a hypodermically accessible fluid infusion port or reservoir, such as that described in U.S. Pat. No. 4,634,443 issued June 18, 1986. A pair of series connected fluid lines 18 and 20 extend through webbing 6 between pressure cushion 4 and respective pressure cushions 2 and 3. Accordingly, a fluid path is established from the fluid source to each of the inflatable pressure cushions 2, 3 and 4 via tubing 17 and fluid lines 18 and 20.

Figure 2:
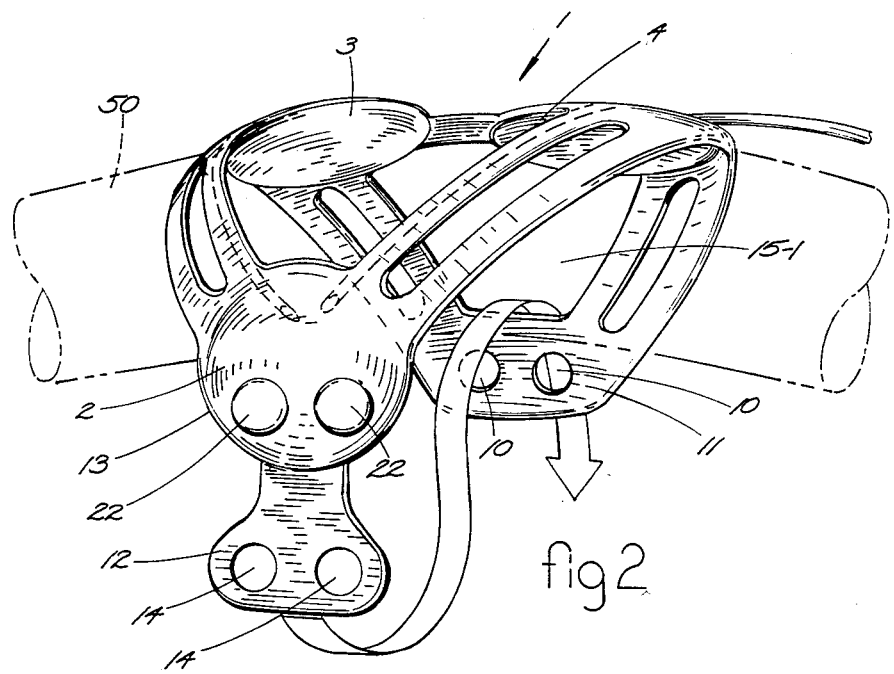
FIGS. 2 and 3 show the technique by which opposite ends of the sphincteric web of FIG. 1 are attached together around a patient's colon.
Figure 3:
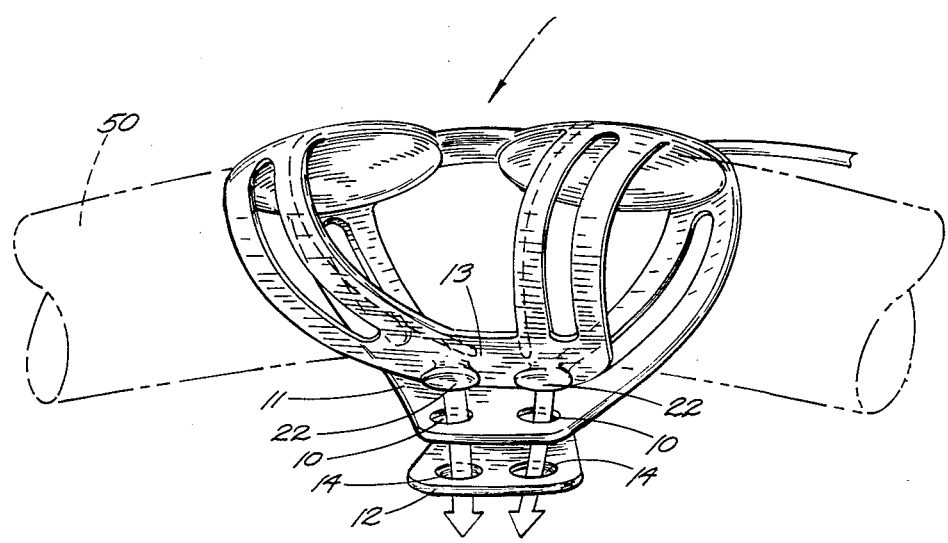

The method by which the sphincteric web 1 embraces a patient's colon (shown in phantom and designated by reference numeral 50) so that the geometry of a normally continent rectum can be artificially replicated is now described while referring to FIGS. 2 and 3 of the drawings. In FIG. 2, the sphincteric web 1 is folded around the colon 50, such that the buttonholes 10 in primary fastening end 11 and the buttonholes in the secondary fastening end 13 lie adjacent one another below the patient's colon 50. As is best shown in FIG. 2, a pair of buttons 22 projects upwardly from the top of pressure cushion 2.

To interconnect the primary and secondary fastening ends 11 and 13 of the sphincteric web 1 so that the web will completely surround the patient's colon 50, the closure tab 12 at the secondary fastening end 13 is pulled through the primary opening 15-1 in the primary fastening end 11 in a direction indicated by the reference arrow 24. Closure tab 12 is positioned behind the primary fastening end 11, such that the buttonholes in tab 12 and primary fastening end 11 are aligned with one another.

As is best shown in FIG. 3, the primary fastening end 11 is rotated into engagement with the pressure cushion 2, and the buttons 22 of cushion 2 are moved through the buttonholes 10 in primary fastening end 11, whereby to attach primary fastening end 11 to secondary fastening end 13. Next, the closure tab 12 is rotated over primary fastening end 11, and the buttons 22 of pressure cushion 2 (which extend through the button holes 10 in primary fastening end 11) are also moved through the buttonholes 14 in tab 12, whereby to secure the closure tab 12 over the primary fastening end 11.

By virtue of the buttons 22 and the buttonholes 10 and 14, interlocking means are provided by which the primary and secondary fastening ends 11 and 13 of sphincteric web 1 may be reliably connected together. The optional closure tab 12 provides a redundant locking feature which, with the cooperation of primary fastening end 11, ensures that the primary and secondary fastening ends 11 and 13 of sphincteric web 1 will not be accidentally detached from one another after the implant surgery has been completed. However, in some cases, it may be desirable to eliminate locking tab 12, altogether, whereby the primary and secondary fastening ends 11 and 13 of sphincteric web 1 are connected together solely by means of buttons 22 and buttonholes 10.

Figure 4:
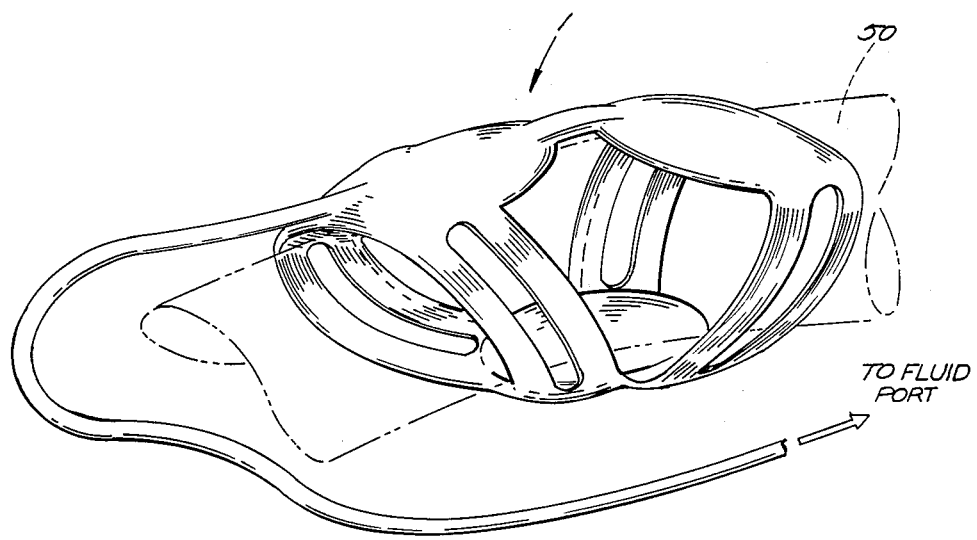
FIGS. 4 and 5 show the sphincteric web surrounding and embracing the patient's colon.
Figure 5:
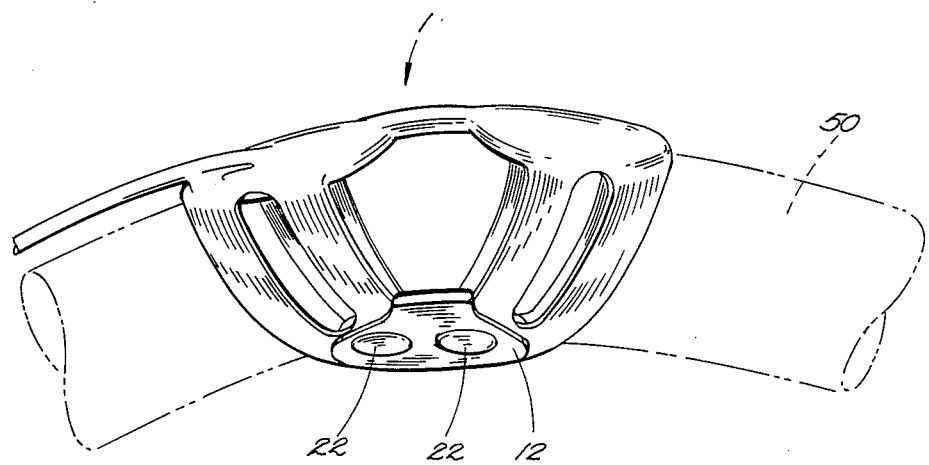

FIGS. 4 and 5 of the drawings show the sphincteric web 1 surrounding and embracing the patient's colon 50. It is to be understood that the horizontal alignment of web 1 and colon 50 in FIGS. 4 and 5 is for purposes of illustration only. In actuality, the sphincteric web 1 and colon 50 generally extend in vertical alignment with one another through the patient's body (in the manner depicted in FIG. 9).

Figure 6:
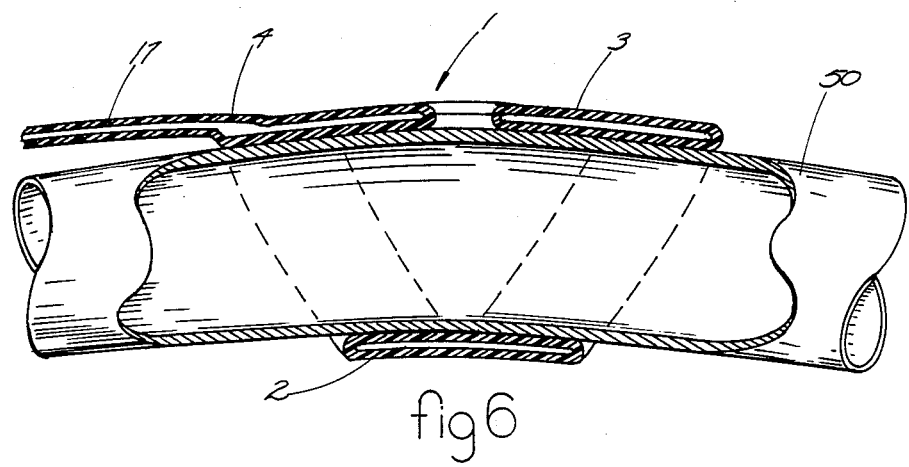
FIGS. 6-8 illustrate the technique by which the pressure cushions of the sphincteric web are inflated to deflect the patient's colon and return the patient to continence.
Figure 7:
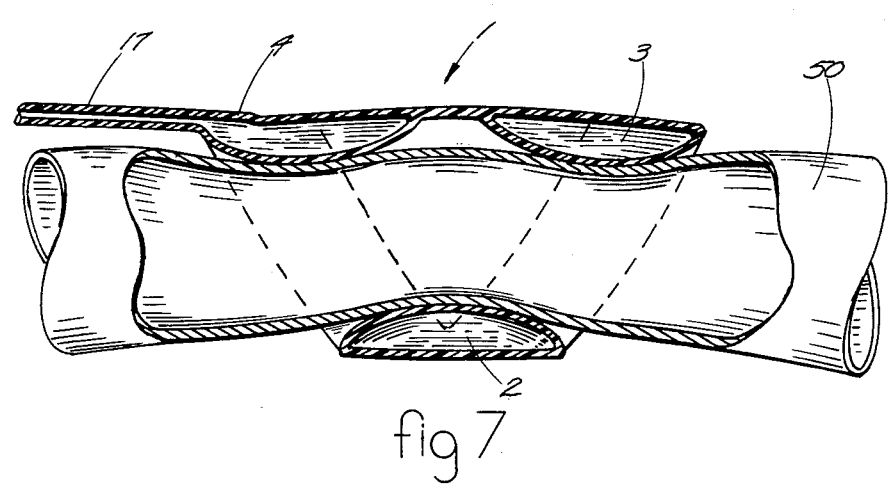
Figure 8:
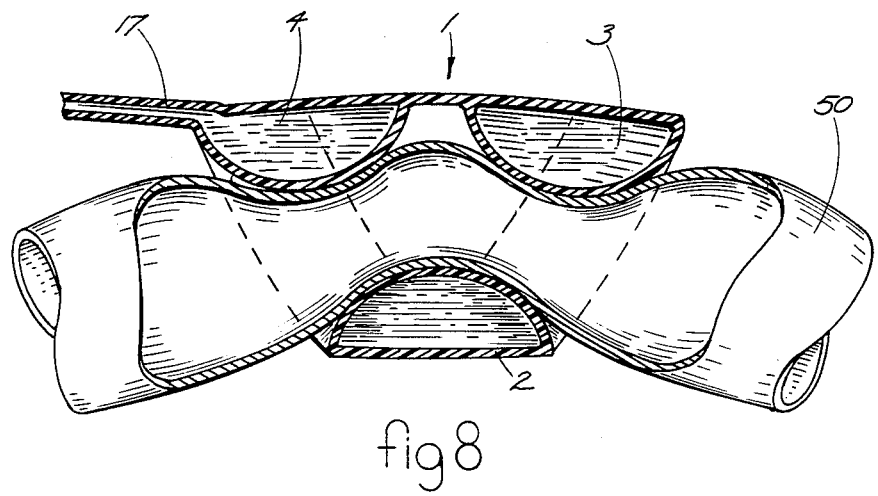

The operation of sphincteric web 1 is now decribed while referring to FIGS. 6, 7 and 8 of the drawings. FIG. 6 shows the web 1 at rest with the inflatable pressure cushions 2, 3 and 4 deflated. However, the fluid circuit including pressure cushions 2, 3 and 4 and hydraulic tubing 17 may be initially filled with minimal fluid to equalize the internal and atmospheric pressures. Accordingly, the patient's colon 50 is relaxed (i.e., neither deflected nor restricted) so that waste material may pass freely therethrough.

In FIG. 7, hydraulic fluid is applied from the source thereof via tubing 17, to a first of the pressure cushions 4 of sphincteric web 1. As previously disclosed when referring to FIG. 1, pressure cushion 4 communicates with pressure cushions 2 and 3 by way of a pair of series connected fluid lines (designated 18 and 20 in FIG. 1). Therefore, fluid is transferred from cushion 4 to cushions 2 and 3, whereupon each of the pressure cushions 2-4 begins to inflate. In FIG. 8, the pressure cushions 2-4 of sphincteric web 1 are fully inflated. In the fully inflated condition, each cushion assumes a hemispheric configuration by which to apply successive deflective forces to the patient's colon 50 for the purpose of deflecting the colon and restricting the movement of material therethrough. Of course, the pressure cushions 2, 3 and 4 may be deflated by withdrawing fluid from the cushions to the source by way of tubing 17, whereby to return colon 50 to the non-deflected, non-restricted condition.

Figure 9:
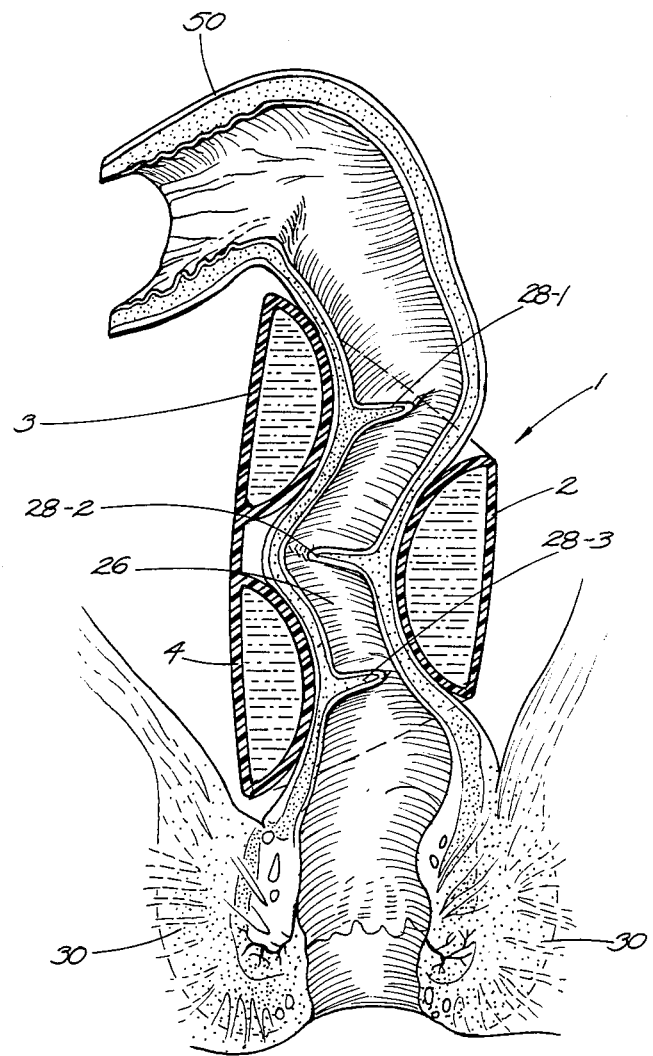
FIG. 9 is an anatomical drawing illustrative of the sphincteric web relative to the colon and rectum of a healthy anatomy.

Referring now to FIG. 9 of the drawings, the sphincteric web 1 is shown surrounding and embracing the rectum 26 of a healthy, normally continent patient.

FIG. 9 is provided to show the disposition and relationship of web 1 to the healthy anatomy. That is to say, the pressure cushions 2-4 of web 1 are particularly positioned to artificially replicate the geometry of a normally continent rectum so as to return an incontinent patient to continence by closely mimicing the three valvular deflections produced by the patient's rectal valves 28-1, 28-2 and 28-3.

Thus, when the pressure cushions 2-4 are inflated, the deflective forces produced thereby are directed in respective planes which are aligned transversely to the orientation of the colon. The pressure cushions 2-4 are spaced longitudinally from one another, such that no two of the deflective forces are applied to the colon in the same plane. Such non-coplanar forces establish the deflection of the colon to restrict the movement of material therethrough.

In the case of a colostomy or ileostomy patient, both the rectum 26 and the continence producing rectal valves 28-1, 28-2 and 28-3 thereof are typically excised. Therefore, sphincteric web 1 preferably surrounds and embraces the patient's colon 50 as a means for enabling the patient to overcome incontinence. In other cases where, due to sphincteric dysfunction, urological damage, trauma, age, catastrophic injury, or the like, either the natural sphincter muscles 30 of the patient are removed and/or the rectal valves are rendered functionally inoperative, the sphincteric web 1 preferably surrounds and embraces the patient's rectum 26 (as shown) to augment or assist any remaining natural sphincteric and/or valvular function to achieve patient continence.

Thus, regardless of whether the sphincteric web 1 surrounds the patient's rectum 26 or colon 50, inflating the pressure cushions 2, 3 and 4 artificially and prosthetically produces axial deflective forces which closely replicate the natural valvular deflections produced by the rectal valves 28-1, 28-2 and 28-3 in a healthy anatomy. The deflective forces produced by sphincteric web 1 cause increased resistance to the flow of material through the rectal or colon, whereby to return the patient to continence.

By virtue of the present sphincteric web 1, a colostomy or ileostomy patient may be prosthetically returned to continence through the application of axially deflective forces rather than potentially damaging obstructive forces. More particularly, the deflecting or bending of the patient's colon (or rectum) as caused by inflating pressure cushions 2-4 restricts material flow according to a non-planar geometry instead of constricting material flow according to a planar geometry, as is undesirably characteristic of conventional occlusive force-generating sphincteric devices. In other words, instead of achieving continence by squeezing the colon to create an obstruction, sphincteric web 1 returns the patient to continence by deflecting the colon while avoiding the possibility of strangulation. Therefore, a patient receiving sphincter web 1 is less likely to be susceptible to hypertrophy, ischemia, necrosis and/or erosion because of the non-planar deflective manner in which continence is achieved.

It will be apparent that while a preferred embodiment has been shown and described, various modifications and changes may be made without departing from the true spirit and scope of the invention.

Having thus set forth a preferred embodiment of the invention, what is claimed is:

1. A prosthetic sphincter to surround a passage of the human anatomy for treating incontinence by restricting the movement of material through said passage, said sphincter comprising a plurality of inflatable pressure cushions, each of said cushions located along said sphincter so as to be spaced from one another in a direction corresponding to the longitudinal axis of the passage to be restricted, and means for supplying fluid to said cushions for causing an inflation thereof, said sphincter being arranged with said passage such that an inflation of said cushions causes forces to be applied to said passage in respective planes which are aligned transversely to the longitudinal axis of said passage, with no two forces being applied to said passage in the same plane, so as to establish a deflection of said passage to thereby restrict the movement of material therethrough.

2. The sphincter recited in claim 1, said sphincter comprising a total of three pressure cushions positioned along said passage to correspond with the location of respective ones of the rectal valves of a normally continent rectum in a healthy human anatomy.

3. The sphincter recited in claim 1, having first and second ends and means to detachably connect said first and second ends together to enable said sphincter to surround said passage.

4. The sphincter recited in claim 3, wherein said means to connect includes at least one button located at said first sphincter end and at least one button hole located at said second end, the receipt of said button through said buttonhole detachably connecting said first and second ends together.

5. The sphincter recited in claim 4, wherein said means to connect also includes a closure tab connected to said first sphincter end and having a buttonhole formed therethrough, the button of said first end being received through the buttonhole in said closure tab after said button is first received through the buttonhole in said second sphincter end to provide a redundant closure means for detachably connecting said first and second ends together.

6. The sphincter recited in claim 1, wherein said fluid supplying means includes tubing connected from a source of fluid supply to a first of said plurality of pressure cushions, and fluid lines extending between said first pressure cushion and the remaining pressure cushions of said plurality thereof.

7. A prosthetic sphincter to surround and embrace the colon of an incontinent patient, said sphincter having longitudinal and lateral axes and comprising at least three inflatable compartments, two of said compartments being positioned at opposite sides of said sphincter on said longitudinal axis thereof and the third of said compartments being positioned at one end of said sphincter on said lateral axis in order to replicate the geometry of a normally continent rectum, and means to inflate said inflatable compartments to cause forces to be directed to said colon in respective planes which are aligned transversely to the longitudinal axis of the colon, such that no two forces are applied to the colon in the same plane, said forces acting to restrict the movement of material through the colon and thereby restore the patient to continence.

8. The sphincter recited in claim 7, wherein said inflatable compartments are hemispherically shaped when inflated so as to deflect, rather than constrict, the colon and thereby restrict the movement of material therethrough.

9. The sphincter recited in claim 7, further comprising means to connect opposite sides of said sphincter together so that said sphincter is arranged to completely surround and embrace the colon.

10. The sphincter recited in claim 9, wherein said means to connect includes at least one button located at a first side of said sphincter and at least one buttonhole located at the opposite side, the receipt of said button through said buttonhole connecting said first and second sides together.

* * * * *